United States Patent

Berg et al.

Patent Number: 5,240,567
Date of Patent: Aug. 31, 1993

[54] SEPARATION OF VINYL ACETATE FROM METHYL ACRYLATE BY EXTRACTIVE DISTILLATION

[75] Inventors: Lloyd Berg, 1314 S. Third Ave., Bozeman, Mont. 59715; Randi W. Wytcherley, Bozeman, Mont.

[73] Assignee: Lloyd Berg, Bozeman, Mont.

[21] Appl. No.: 41,868

[22] Filed: Apr. 2, 1993

[51] Int. Cl.$^5$ .................. B01D 3/40; C07C 67/54
[52] U.S. Cl. .................. 203/57; 203/58; 203/60; 203/63; 203/64; 203/65; 203/DIG. 10; 203/DIG. 21; 560/218; 560/248
[58] Field of Search .................. 203/57, 58, 60, 63, 203/64, 65, DIG. 10, DIG.21; 560/248, 218

[56] References Cited

U.S. PATENT DOCUMENTS

| | | | |
|---|---|---|---|
| 2,171,795 | 9/1939 | Kautter | 203/65 |
| 3,691,021 | 9/1972 | Feldman et al. | 560/248 |
| 3,736,236 | 5/1973 | Di Fiore et al. | 560/248 |
| 4,897,161 | 1/1990 | Berg et al. | 203/51 |
| 4,925,533 | 5/1990 | Berg | 203/51 |

FOREIGN PATENT DOCUMENTS

| | | | |
|---|---|---|---|
| 45-36887 | 11/1970 | Japan | 560/218 |
| 47-37929 | 9/1972 | Japan | 560/218 |

*Primary Examiner*—Wilbur Bascomb, Jr.

[57] ABSTRACT

The separation of vinyl acetate from methyl acrylate by distillation is difficult because of the closeness of their boiling points. Vinyl acetate can be readily removed from methyl acrylate by extractive distillation. Typical effective agents are phenol, methoxyethanol and isobutyl vinyl ether.

1 Claim, No Drawings

SEPARATION OF VINYL ACETATE FROM METHYL ACRYLATE BY EXTRACTIVE DISTILLATION

FIELD OF THE INVENTION

This invention relates to a method for separating vinyl acetate from methyl acrylate using certain higher boiling liquids as the agent in extractive distillation.

DESCRIPTION OF PRIOR ART

Extractive distillation is the method of separating close boiling compounds from each other by carrying out the distillation in a multiplate rectification column in the presence of an added liquid or liquid mixture, said liquid(s) having a boiling point higher than the compounds being separated. The extractive agent is introduced near the top of the column and flows downward until it reaches the stillpot or reboiler. Its presence on each plate of the rectification column alters the relative volatility of the close boiling compounds in a direction to make the separation on each plate greater and thus require either fewer plates to effect the same separation or make possible a greater degree of separation with the same number of plates. The extractive agent should boil higher than any of the close boiling liquids being separated and not form minimum azeotropes with them. Usually the extractive agent is introduced a few plates from the top of the column to insure that none of the extractive agent is carried over with the lowest boiling component. This usually requires that the extractive agent boil about twenty Celcius degress or more higher that the lowest boiling component.

At the bottom of a continuous column, the less volatile components of the close boiling mixtures and the extractive agent are continuously removed from the column. The usual methods of separation of these two components are the use of another rectification column, cooling and phase separation, or solvent extraction.

Extractive distillation would be an attractive method of effecting the separation of vinyl acetate from methyl acrylate if agents can be found that (1) will create a large apparent relative volatility between vinyl acetate and methyl acrylate and (2) are easy to recover from the methyl acrylate, that is, form no azeotrope with methyl acrylate and boil sufficiently above methyl acrylate to make separation by rectification possible with only a few theoretical plates.

Extractive distillation typically requires the addition of an equal amount to twice as much extractive agent as the vinyl acetate—methyl acrylate on each plate of the rectification column. The extractive agent should be heated to about the same temperature as the plate into which it is introduced. Thus extractive distillation imposes an additional heat requirement on the column as well as somewhat larger plates. However this is less than the increase occasioned by the additional agents required in azeotropic distillation.

Another consideration in the selection of the extractive distillation agent is its recovery from the bottoms product. The usual method is by rectification in another column. In order to keep the cost of this operation to a minimum, an appreciable boiling point difference between the compound being separated and the extractive agent is desirable. We recommend twenty Celcius degrees or more difference. It is also desirable that the extractive agent be miscible with overhead products otherwise it will form a two phase azeotrope with them and some other method of separation will have to be employed.

Vinyl acetate, B.P.=72.7° C. and methyl acrylate, B.P.=80.3° C. boil so close together that the relative volatility is only 1.3. Table 1 shows that the separation by conventional rectification requires 42 actual plates to get 99% purity. With an agent giving a relative volatility of 1.9, only 20 actual plates are required.

TABLE 1

Theoretical and Actual Plates Required vs. Relative Volatility for Vinyl Acetate - Methyl Acrylate Separation

| Relative Volatility | Theoretical Plates Required At Total Reflux, 99% purity | Actual Plates Required, 75% Efficiency |
| --- | --- | --- |
| 1.3 | 35 | 47 |
| 1.5 | 23 | 31 |
| 1.8 | 16 | 21 |
| 1.9 | 15 | 20 |

OBJECTIVE OF THE INVENTION

The object of this invention is to provide a process or method of extractive distillation that will enhance the relative volatility of vinyl acetate from methyl acrylate in their separation in a rectification column. It is a further object of this invention to identify organic compounds which in addition to the above constraints, are stable, can be separated from methyl acrylate by rectification with relatively few theoretical plates and can be recycled to the extractive distillation column and re-used with little decomposition.

SUMMARY OF THE INVENTION

The objects of this invention are provided by a process for separating vinyl acetate from methyl acrylate which entails the use of certain organic compounds as the agent in extractive distillation.

DETAILED DESCRIPTION OF THE INVENTION

We have discovered that certain organic compounds will greatly improve the relative volatility of vinyl acetate to methyl acrylate and permit the separation of vinyl acetate from methyl acrylate by rectification when employed as the agent in extractive distillation.

TABLE 2

Effective Extractive Distillation Agents

| Compounds | Relative Volatility |
| --- | --- |
| None | 1.3 |
| Adiponitrile | 1.4 |
| Sulfolane | 1.4 |
| Phenol | 1.8 |
| o-Cresol | 1.7 |
| m-Cresol | 1.7 |
| p-Cresol | 1.8 |
| 2,4-Di-tert amyl phenol | 1.6 |
| 2-tert. Butyl phenol | 1.4 |
| 2,6-Dimethyl phenol | 1.6 |
| 4-Ethyl phenol | 1.7 |
| 1-Propanol | 1.4 |
| Propylene glycol phenyl ether | 1.4 |
| Isodecyl alcohol | 1.4 |
| sec. Phenethyl alcohol | 1.4 |
| Cyclopentanol | 1.5 |
| Methoxyethanol | 1.9 |
| Isobutyl vinyl ether | 1.6 |
| Nitrobenzene | 1.4 |

Table 2 lists the compounds that we have found to be effective. They are adiponitrile, sulfolane, phenol, o- cresol, m-cresol, p-cresol, 2-tert. butyl phenol, 2,4-ditert. amyl phenol, 2,6-dimethyl phenol, 1-propanol, 4-ethyl phenol, propylene glycol phenyl ether, isodecyl alcohol, sec. Phenethyl alcohol, cyclopentanol, isobutyl vinyl ether, methoxyethanol and nitrobenzene.

THE USEFULNESS OF THE INVENTION

The usefulness or utility of this invention can be demonstrated by referring to the data presented in Tables 1 and 2. All of the successful agents show that vinyl acetate can be separated from methyl acrylate by means of extractive distillation in a rectification column and that the ease of separation as measured by relative volatility is considerable.

WORKING EXAMPLES

Example 1

Fifty grams of vinyl acetate, 50 grams of methyl acrylate and 50 grams of phenol were charged to an Othmer type vapor-liquid equilibrium still and refluxed for thirteen hours. Analysis of the vapor and liquid by gas chromatography gave a vapor composition of 57.4% vinyl acetate, 42.6% methyl acrylate and a liquid composition of 43.3% vinyl acetate, 56.7% methyl acrylate. This indicates a relative volatility of 1.8.

Example 2

Fifty grams of vinyl acetate, 50 grams of methyl acrylate and 50 grams of methoxyethanol were charged to the vapor-liquid equilibrium still and refluxed for three hours. Analysis gave a vapor of 67% vinyl acetate, 33% methyl acrylate and a liquid composition of 51.3% vinyl acetate, 48.7% methyl acrylate. This indicates a relative volatility of vinyl acetate to methyl acrylate of 1.9.

We claim:

1. A method for recovering vinyl acetate from a mixture of vinyl acetate and methyl acrylate which comprises distilling a mixture of vinyl acetate and methyl acrylate in a rectification column in the presence of about one part of an extractive agent per part of vinyl acetate - methyl acrylate mixture, recovering the vinyl acetate as overhead product and the methyl acrylate and the extractive agent from the stillpot, wherein said extractive agent consists of one material selected from the group consisting of adiponitrile, sulfolane, phenol, o-cresol, m-cresol, p-cresol, 2-tert. butyl phenol, 2,4-ditert. amyl phenol, 2,6-dimethyl phenol, 4-ethyl phenol, 1-propanol, isodecyl alcohol, sec. phenethyl alcohol, cyclopentanol, methoxyethanol, propylene glycol phenyl ether, isobutyl vinyl ether and nitrobenzene.

* * * * *